US007988681B2

(12) United States Patent
McGarity et al.

(10) Patent No.: US 7,988,681 B2
(45) Date of Patent: Aug. 2, 2011

(54) PORTABLE RAPIDLY DEPLOYABLE WASTE CONTAINMENT DEVICE

(75) Inventors: Kermetta M McGarity, Flowery Branch, GA (US); Howard C McGarity, Jr., Flowery Branch, GA (US)

(73) Assignees: Kermetta M. McGarity, Flowery Branch, GA (US); Howard C. McGarity, Flowery Branch, GA (US)

( * ) Notice: Subject to any disclaimer, the term of this patent is extended or adjusted under 35 U.S.C. 154(b) by 0 days.

(21) Appl. No.: 12/653,711

(22) Filed: Dec. 17, 2009

(65) Prior Publication Data

US 2010/0234819 A1 Sep. 16, 2010

Related U.S. Application Data

(60) Provisional application No. 61/210,001, filed on Mar. 13, 2009.

(51) Int. Cl.
*A61M 1/00* (2006.01)

(52) U.S. Cl. ........ 604/317; 604/321; 604/327; 604/346; 604/355; 220/9.1; 220/9.3; 220/9.4; 383/4; 383/6; 383/14; 383/22; 383/24; 383/33; 383/35; 383/61.4; 383/73; 383/74; 383/76; 383/108; 383/109; 383/113; 383/114; 383/200; 383/206

(58) Field of Classification Search .................. 604/317, 604/321, 327, 346, 355; 220/9.1, 9.3, 9.4; 383/4, 6, 61.4, 73, 74, 76, 14, 22, 24, 33, 383/35, 108, 109, 113, 114, 200, 206
See application file for complete search history.

(56) References Cited

U.S. PATENT DOCUMENTS

| | | | | | |
|---|---|---|---|---|---|
| 665,942 | A | * | 1/1901 | Tabler | 383/74 |
| 1,691,904 | A | * | 11/1928 | Gamble | 206/8 |
| 2,943,660 | A | | 7/1960 | Seeger | |
| 3,475,767 | A | | 11/1969 | Friesen | |
| 3,653,583 | A | | 4/1972 | Meyer | |
| 3,675,667 | A | * | 7/1972 | Miller | 135/126 |
| 3,738,567 | A | | 6/1973 | Ruda | |
| 4,388,739 | A | * | 6/1983 | Martinon et al. | 8/150 |
| 4,515,300 | A | | 5/1985 | Cohen | |
| 4,546,877 | A | | 10/1985 | Evans | |
| 4,610,039 | A | | 9/1986 | Stern | |
| 4,687,036 | A | | 8/1987 | Thomas | |
| 4,815,640 | A | | 3/1989 | Johnson | |
| 4,825,892 | A | * | 5/1989 | Norman | 135/126 |
| 4,878,764 | A | | 11/1989 | Meyer | |
| 4,944,393 | A | | 7/1990 | Cappuzzo | |
| 4,951,333 | A | * | 8/1990 | Kaiser et al. | 5/417 |
| 4,964,188 | A | * | 10/1990 | Olson | 15/227 |
| 4,979,833 | A | | 12/1990 | Cook | |
| 5,022,767 | A | * | 6/1991 | Cardulla | 383/33 |
| 5,038,812 | A | * | 8/1991 | Norman | 135/126 |
| 5,044,774 | A | | 9/1991 | Bullard | |
| 5,092,681 | A | | 3/1992 | Ashley, III | |
| 5,118,201 | A | | 6/1992 | Cook | |
| 5,133,607 | A | | 7/1992 | Bonke | |

(Continued)

*Primary Examiner* — Melanie J Hand
*Assistant Examiner* — Ginger T Chapman

(57) ABSTRACT

The present invention relates to a portable waste containment device that is rapidly deployable. The waste containment device allows containment of liquid or semi-liquid waste until permanently disposed. The present invention also provides a portable waste containment system wherein the waste containment device is enclosed within a package for storage and when pulled from the package the waste containment device is ready for use. Still further, the present invention provides a method of using the portable waste containment device of the present invention.

15 Claims, 8 Drawing Sheets

U.S. PATENT DOCUMENTS

| | | | | |
|---|---|---|---|---|
| 5,137,044 | A * | 8/1992 | Brady | 135/126 |
| 5,160,196 | A | 11/1992 | Curtis | |
| 5,213,147 | A * | 5/1993 | Zheng | 160/370.21 |
| 5,279,539 | A | 1/1994 | Bohan | |
| 5,346,311 | A | 9/1994 | Siler | |
| 5,358,440 | A * | 10/1994 | Zheng | 446/48 |
| 5,393,023 | A * | 2/1995 | Callan | 248/97 |
| 5,403,050 | A | 4/1995 | Searing | |
| 5,417,354 | A | 5/1995 | Jones | |
| 5,429,437 | A * | 7/1995 | Shaw et al. | 383/33 |
| 5,647,372 | A | 7/1997 | Tovey | |
| 5,692,660 | A | 12/1997 | Stewart | |
| 5,845,994 | A | 12/1998 | Rice | |
| 5,964,533 | A * | 10/1999 | Ziglar | 383/36 |
| 6,302,583 | B1 | 10/2001 | Steinmetz | |
| 6,520,365 | B2 * | 2/2003 | Schneider | 220/9.2 |
| 6,547,436 | B2 | 4/2003 | Sutton | |
| 6,554,810 | B1 | 4/2003 | Wilk | |
| 6,564,838 | B1 | 5/2003 | Cruickshank | |
| 6,783,016 | B2 * | 8/2004 | Wang | 220/9.2 |
| 6,948,632 | B2 * | 9/2005 | Kellogg et al. | 220/9.4 |
| 6,991,333 | B2 | 1/2006 | Van Atta | |
| 7,073,942 | B2 * | 7/2006 | Vazquez | 383/2 |
| 7,137,736 | B2 | 11/2006 | Pawloski | |
| 7,237,753 | B2 * | 7/2007 | Metcalfe | 248/99 |
| 7,308,989 | B2 * | 12/2007 | Zheng | 220/9.2 |
| 7,344,022 | B2 | 3/2008 | Madson | |
| D589,141 | S * | 3/2009 | McClellan et al. | D24/121 |
| 7,500,893 | B2 | 3/2009 | Arias | |
| 7,520,673 | B2 | 4/2009 | Bonke | |
| D605,817 | S * | 12/2009 | LeCoq | D30/129 |
| 7,815,372 | B2 * | 10/2010 | Stanton et al. | 383/104 |
| 2001/0007934 | A1 * | 7/2001 | Smith | 604/346 |
| 2003/0128897 | A1 * | 7/2003 | Lehrman | 383/2 |
| 2004/0112908 | A1 * | 6/2004 | Tillmann et al. | 220/666 |
| 2005/0201642 | A1 | 9/2005 | Terry | |
| 2005/0249439 | A1 | 11/2005 | Penson | |
| 2005/0261644 | A1 | 11/2005 | Fields | |
| 2006/0059644 | A1 | 3/2006 | Steele | |
| 2006/0070178 | A1 | 4/2006 | Taheri | |
| 2006/0204149 | A1 | 9/2006 | Guerra | |
| 2006/0265950 | A1 | 11/2006 | Castleberry | |
| 2007/0253648 | A1 * | 11/2007 | Austin et al. | 383/104 |
| 2008/0101731 | A1 * | 5/2008 | Carlson | 383/41 |
| 2008/0229499 | A1 | 9/2008 | Narboni-Campora | |
| 2008/0310767 | A1 | 12/2008 | Engel | |

* cited by examiner

PORTABLE RAPIDLY DEPLOYABLE WASTE CONTAINMENT DEVICE

CROSS-REFERENCE TO RELATED APPLICATIONS

This application claims priority to U.S. Provisional Patent Application Ser. No. 61/210,001, filed Mar. 13, 2009, which application is incorporated herein in its entirety by this reference.

FIELD OF THE INVENTION

The present invention relates to a portable waste containment device that is rapidly deployable. The waste containment device allows containment of liquid or semi-liquid waste until permanently disposed. The present invention also provides a portable waste containment system wherein the waste containment device is enclosed within a package for storage and when removed from the package the waste containment device is ready for use. Still further, the present invention provides a method of making the portable waste containment device of the present invention.

BACKGROUND OF THE INVENTION

Most people will experience vomiting episodes during their lifetimes. For some people, such as those who are chronically ill or who might be undergoing chemotherapy, vomiting may be a daily or almost daily occurrence. For other people, vomiting episodes will occur during periods of illness or, for some women, during pregnancy. People of all ages and health, especially children, may experience motion sickness when traveling. While the reasons and frequency of vomiting episodes may differ among people, afflicted persons typically need quick access to a receptacle to capture their waste in order to not soil their surroundings. These people also need a ready and hygienic way to dispose of their waste. If the person is not near a waste receptacle at the time of their vomiting episode, they may also need to store the waste for a period of time.

The traditional way to capture vomit is to use a "sickness bag." These bags, which are common in places where motion sickness typically occurs (e.g., airplanes and ships), require the user to open and hold the bag during a vomiting episode. While useful to capture vomit, these bags can be difficult and slow to open, and they do not generally provide a hygienic seal. These bags also do not possess structure that allows the bag to remain in a suitable open position so that a sick person does not need to worry about maintaining an opening at the same time he or she is having a vomiting episode. Moreover, these bags do not have an opening sized and shaped to allow a person who is about to be sick to easily "aim" into the bag so as to reduce the possibility that the vomit will spill outside the bag. Still further, traditional sickness bags are not generally sized and shaped to allow easy storage and portability. Such sickness bags do not lend themselves to be carried around until needed, such as in a pocket or a purse. Because most people cannot predict when and where they may become sick, few people would desire to carry traditional sickness bags around until needed for use.

There have been attempts to provide improvements over traditional sickness bag. These include variations on the traditional sickness bag such as that disclosed in U.S. Pat. No. 7,344,022, the disclosure of which is incorporated herein in its entirety by this reference. Other forms of sickness bags address ways to attach a bag to a frame so as to allow a sick person to vomit into a stabilized bag. These frame-type solutions are disclosed, for example, in U.S. Pat. Nos. 2,943,660, 6554,810 and 6,991,333 and US Patent Publication Nos. 2008/0310767 and 2005/0261644, disclosures of which are each incorporated in their entirety by this reference. Notwithstanding the many variations of sickness bags in the prior art, the inventors herein have found that none of these solutions provides a product that is readily portable, easily storable and quickly deployable as would be needed by a sick person.

In addition to there being an improved way to collect and hygienically contain vomit, it would also be desirable to provide improvements to provide portable and quickly deployable waste containers to hygienically collect and store for disposal other forms of unpleasant and, in many cases, biohazard material.

The present invention provides these, as well as other, needed benefits.

SUMMARY OF THE INVENTION

The present invention comprises a portable waste containment device that provides a number of beneficial features such as speedy deployment by a user and an opening suitably large to allow ready use by a person who needs to vomit. The waste containment device of the present invention is highly suitable for such use because the mouth maintains its open position with little or no effort on the part of a user. Still further, the waste containment device of the present invention allows vomit or other waste material to be hygienically enclosed in the waste containment device.

In particular aspects, the waste containment device of the present invention comprises a foldable ring that is moveable between an open configuration when the ring is unfolded and a storage configuration when the ring is folded. The foldable ring is attached to a substantially water impermeable material, such as plastic, so as to provide a container suitable for collecting and holding liquid or semi-liquid waste when the ring is in the open configuration. The present invention also provides a portable waste containment system wherein the waste containment device is enclosed within a package for storage and when pulled from the package the waste containment device is ready for use. Still further, the present invention provides a method of making the portable waste containment device of the present invention.

Additional advantages of the invention will be set forth in part in the description that follows, and in part will be apparent from the description, or may be learned by practice of the invention. The advantages of the invention will be realized and attained by means of the elements and combination particularly pointed out in the appended claims. It is to be understood that both the foregoing general description and the following detailed description are exemplary and explanatory only and are not restrictive of the invention, as claimed.

DETAILED DESCRIPTION OF THE INVENTION

Figure 1:
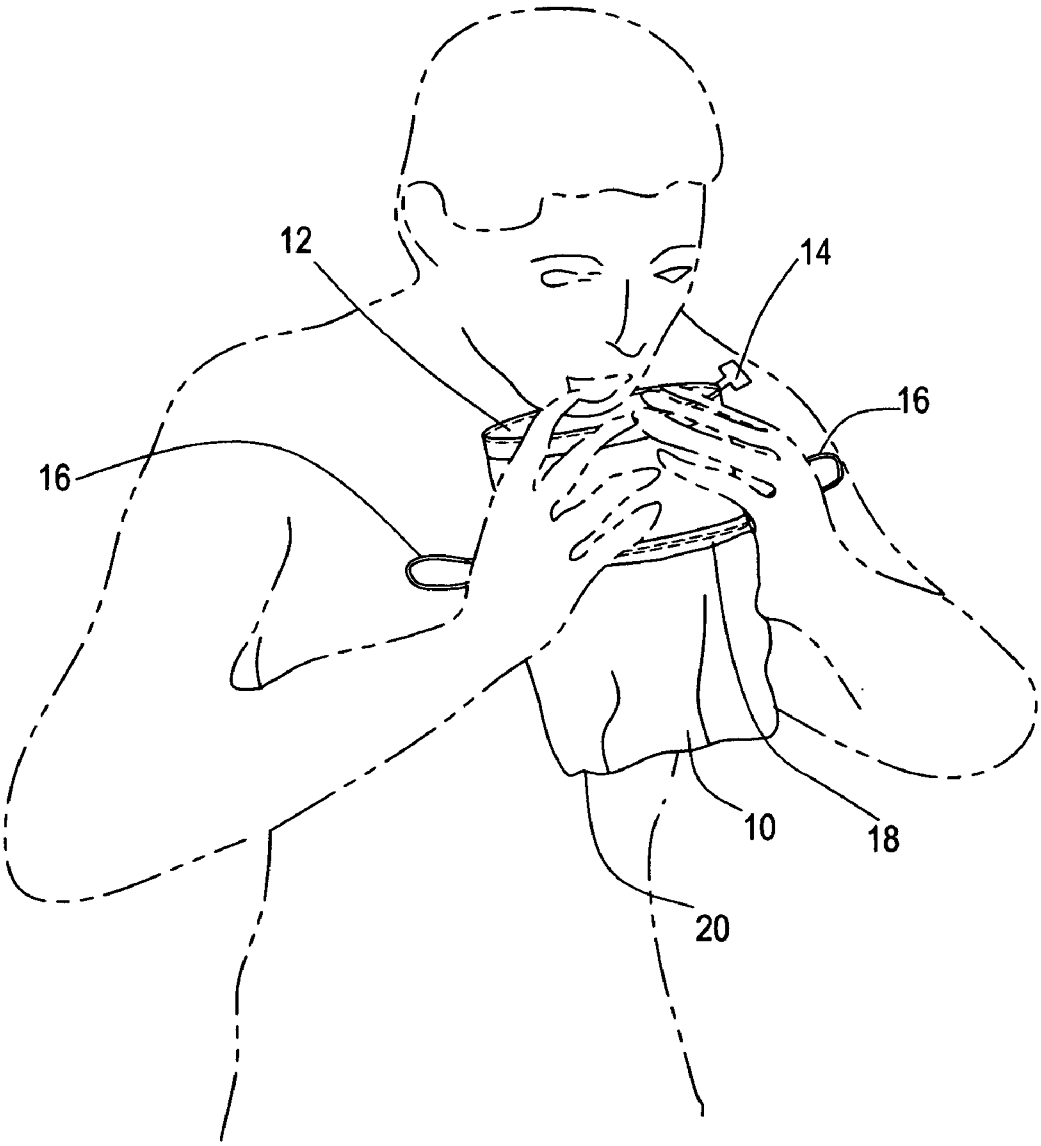
FIG. 1 illustrates the manner in which the waste containment device of the present invention can be used during a vomiting episode.

The present invention may be understood more readily by reference to the following detailed description of preferred embodiments of the invention and the Examples included therein and to the Figures and the previous and following description. It is also to be understood that the terminology used herein is for the purpose of describing particular aspects only and is not intended to be limiting.

It must be noted that, as used in the specification and the appended claims, the singular forms "a," "an" and "the" include plural referents unless the context clearly dictates otherwise.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In one aspect, the present invention comprises a rapidly deployable waste containment device. Still further, the waste containment device of the present invention is readily portable. The waste containment device of the present invention comprises a mouth (or opening) that, after deployment of the device by a user, maintains its open position to provide an easy target for a user who needs to vomit or for the containment of other forms of waste. In a further aspect, the waste containment device of the present invention is sealable so as to allow hygienic containment of waste.

As contemplated herein, the term "waste" includes, but is not limited to, vomit, bloody clothes or tissues from nosebleeds and the like, soiled feminine hygiene products, dirty diapers, human and dog excrement, urine, spit, sticky candy, melting ice cream or garbage. However, the present invention is not limited by being able to contain the listed waste types. In addition to these and other waste materials, the present invention could also suitably be used to hold specimens collected in the field (e.g., including botanical, zoological, plants, insects etc.) or comparable "non waste" materials. For ease of reference, the present invention is referred to as a "waste containment device" herein.

In one aspect, the present invention comprises a foldable ring that, when unfolded, forms the circumference of the waste containment device when it is in a deployed state (that is, when it is ready for use). The foldable ring may be provided as one continuous loop, or may be a strip or strips of material connected at the ends to form the circumference, which can also be referred to as a "loop" or "hoop". The ring may be circular or oval, as long as such shape is suitable to allow suitable storage and deployment.

The foldable ring can be formed from a flexible metal, plastic or a composite thereof. The foldable ring should comprise a material that is relatively strong, and yet is flexible to a sufficient degree to allow it to be folded over on itself. In use, the foldable ring can assume two configurations.

In a storage configuration, the foldable ring is collapsed (or folded) into a size that is considerably smaller than its open configuration. This storage configuration is favorably small to allow ready portability of the waste containment device, such as in a package as discussed hereinafter. In one illustrative example of the small size of the present invention, when collapsed, the waste containment device of the present invention can fit into a package that is about 4 inches by about 3 inches. However, when expanded, the waste containment device that fits into that package has a mouth opening of about 5, 6, 7 or 8 inches in diameter. As would be realized, the folded size of the foldable ring is generally about ½ of the size of the open diameter for a round opening.

When the waste containment device is folded into the storage configuration, potential energy is suitably stored therein. When deployed from the storage configuration, this potential energy forces the foldable ring to unfold. In this second position, which is the deployed configuration, the unfolded ring forms a circumference for the waste containment device, which, when attached to a bag as described hereinafter, allows the device to be used to collect vomit or other forms of waste when a bag or the like is attached.

A significant improvement in the present invention is that the waste containment device maintains its structure after the ring unfolds. The user need only hold onto the waste containment device at the circumference to provide a suitable target for his or her vomit. In other words, the mouth, (or target), of the waste containment device possesses structure and there is little or no need for the other aspects of the waste containment device to possess structure in order to make the device suitable for its intended use. As will be recognized, the structure of the mouth of the waste containment device of the present invention is wholly or substantially independent of any frame along the sides or bottom of the waste containment device. Accordingly, in one or more aspects, the waste containment device of the present invention does not comprise a frame. Still further, the waste containment device of the present invention comprises structure substantially only in the area of the mouth. As used herein, "structure" means the ability of the waste containment device to remain open without external or internal support other than that provided by the circumference.

Because the foldable ring must be readily deployable from a folded to an unfolded position (or from a storage to a use position) when needed by a user, it is currently believed that the foldable ring should be prepared from a material that comprises "memory." That is, when the waste containment device is deployed by a user, the foldable ring should be able to substantially return to the shape in which it was originally configured, that is, to form the circumference of the waste containment device. Moreover, the ring should unfold quickly to be ready to be deployed in a short period of time. At this time, the inventors believe that aluminum, steel, stainless steel, plastics and composite materials will be suitable for use herein. However, it is contemplated that any other material exhibiting the characteristics needed for the foldable ring will be suitable for use in the waste containment device.

The foldable ring can be fabricated by joining two ends of a length of suitable material to form the circumference for the waste containment device. The ends can be attached by a connector (such as by a slip connector or the like) or the ends can be welded or glued. At this time, it is believed that the form of attachment needs only to be suitable for the particular material from which the foldable ring is made. However, whatever form of attachment is used, the attachment must be appropriate to allow the waste containment device to be stored for an extended period of time and to allow it to be suitably deployed for use when needed.

The length of material used to form the circumference when the ends are attached should be suitable to provide an opening of the waste containment device that allows a user to readily deposit the waste material into the interior substantially without spillage. In the case of a person using the waste containment device to collect vomit, it would be understood that the person will likely be in serious discomfort and, and as such, will be in little condition to "aim." The circumference of the waste containment device that is formed from the foldable ring should therefore be large enough to allow a user to place the waste containment device over his or her mouth quickly and without much effort. In one aspect, the circumference material has a length suitable to provide a circumference (or waste containment device mouth) of from about 4 to about 8 inches or any other suitably sized mouth for the intended use. As one would recognize, the length of the material needed to provide a particular circumference is defined by well-known mathematical relationships, and as such need not be described in detail herein. By way of illustration, when the waste containment device of the present invention comprises a diameter of 6 inches, the length of material used is about 19 inches.

However, since the waste containment device is suitable for use to collect and dispose of many other materials than vomit, it should be understood that the present invention is not limited to the lengths and circumferences stated herein, as long as the foldable ring structure is utilized therein.

To provide the waste containment device, a suitable material is attached to a foldable ring. The material should be impervious to water in general and, specifically, to water-containing waste. The containment material is therefore suitably plastic. Suitable forms of plastic comprise LDPE, MDPE, HDPE and the like. A useful type of plastic is a monolayer polyethylene film of 1 mil thickness. (Bloomer Plastics, Inc, Bloomer Wis.). The thickness of the plastic used in the present invention can be from about 0.5 to about 6 mils or from about 1 to about 3 mils or, in some aspects, thicker or thinner. The thickness of the plastic is determined by the functional properties of the waste containment device of the present invention. As such, any thickness can be used as long as the beneficial aspects of the present invention are achieved. In this regard, the inventors have found that lightly embossing can reduce bulk density for a given thickness of plastic and allows the material to drape well and compact more easily. Biodegradable plastic may also be used, as long as such material is suitably impervious to water-containing waste for a period of time to allow vomit and the like to be contained without degradation prior to disposal. For example, in the case of car motion sickness, it may be several minutes before the contained vomit can be disposed of properly. In further aspects, the containment material can be a fabric that has been coated to make it substantially water impervious.

The containment material is suitably configured to form a bag. In this regard, a single sheet of plastic or fabric having a first side and a second side can be folded and the ends brought together. The two open ends (that is, the side and the bottom) can then be sealed (such as with glue, heat sealing or the like) to form a bag. Alternatively, the bag can be formed from two or more pieces of plastic whereby the various pieces are brought together and glued end to end to form a single bag, sealed or otherwise attached to form a water impervious seal. When fabric is used, the bag can be formed similarly, except that other suitable forms of forming a water impervious seal (such as sewing) can be used.

The bag can be attached to the foldable ring in a number of ways. In one aspect, the open portion of the bag can be folded over the top of the foldable ring and suitably attached to the body thereof. Alternatively, a sleeve can be formed to allow placement of the foldable ring so as to provide a closeable mouth on the waste containment device. In this aspect, a top portion can be formed from a length of material, which is suitably identical to that from which the bag is formed. The second end of the top portion can overlay the open end (that is, the "mouth") of the bag and the second end of the top portion. These ends can then be suitably attached to each other. The second end of the top portion can be oriented to the exterior of the waste containment device and the top portion of the bag can be oriented to the interior of the waste containment device or vice versa.

In the sleeve configuration, the foldable ring can be attached by placing the foldable ring in between the first portion of the bag and the second portion of the top portion prior to sealing the pieces together. Alternatively, the material used to form the foldable ring can be threaded through the sleeve after the top portion and bag and the ends of the material can be connected when the ends thereof exit an opening in the sleeve so as to provide the foldable ring.

Since the waste containment device is, in primary aspects, intended for use to collect and contain waste materials, which will likely be somewhat noxious or, in many instances, a biohazard, it can be highly desirable for the user to be able to seal the waste containment device after the waste material is placed therein. In this regard, the inventors herein have found that an engageable closure can be integrated into the waste containment device to provide a substantially leak proof seal.

In one aspect, a drawstring forms the engageable closure. This drawstring can be formed from folding over the first end of the top portion of the waste containment device to form a sleeve upon attachment of the first end to the body of the waste containment device. A length of string is either present in the sleeve portion prior to formation of the sleeve or the string can be threaded through the sleeve after it is formed. A drawstring mechanism will accordingly be formed on the top of the waste containment device. It has been discovered that, when engaged, this drawstring can allow the waste containment device to contain and store the waste therein with a substantially leak-proof seal.

In a further aspect, when the foldable ring is located at a the top of the waste containment device (in contrast to being incorporated along the body of thereof), the drawstring can be formed by overlapping and attaching the first portion of the bag to the second portion of the top portion to form a sleeve through which the drawstring can be employed. As will be recognized, the string or thread for the drawstring can be placed in the sleeve formed therefrom prior to or after formation of the sleeve. Yet further, the waste containment device can have strings or tape attached suitably attached to the outside thereof, wherein the string or tape can be used to seal the waste containment device after used. In these aspects, the string or tape can be pulled around the body of the waste containment device to provide a substantially leakproof seal.

The waste containment device of the present invention provides significant improvements over the emesis receptacle of US Patent Publication No. 2005/061644, the disclosure of which was previously incorporated herein in its entirety by this reference. Specifically, the container disclosed in the '644 publication comprises a coiled spring that serves a supporting structure for the collapsible structure therein. The present invention with its foldable ring, as opposed to a frame supporting the entire receptacle, is a much simpler way to provide a quickly deployable waste containment device. The present invention is also an improvement over the invention described in US Patent Publication No. 2008/0310767, also previously incorporated by reference, which describes a collapsible emesis receptacle formed from a spring. As shown by the FIGS. 2 and 3 in regards to the arm shown therein, the emesis container of the '767 publication is quite large and could not be easily carried in a purse or pocket.

The deployment means of the present invention, in significant aspects, can be visualized as akin to a parachute ripcord. Specifically, when needed, the waste containment device of the present invention must be ready for immediate use and is expected by the user to function appropriately. Accordingly, when the user opens the package, the tab, pull or the like should be readily visible for activation. The tab, pull or the like should allow the undeployed waste containment device to be quickly removed from the package at such time the waste containment device of the present invention immediately or almost immediately opens for use.

In a further aspect, the present invention comprises a system to contain waste, in particular vomit or other liquid or semi-liquid human or animal waste. In this aspect, the system comprises the waste containment device as discussed hereinabove and a package wherein the waste containment device can be stored for use in a portable manner and is also readily deployable for use. The invention comprises a package that is suitably sized to contain the waste containment device for storage and to allow the waste containment device to be quickly removed for deployment and use. The package can be an envelope or sleeve or it can be a carrier. The package can comprise paper, plastic or fabric or a combination thereof. In use, the user (who might be under considerable distress due to a need to vomit) need only open the package and remove the waste containment device therefrom by grabbing the foldable ring and pulling the waste containment device out of the package. Upon removal from the package, the waste containment device immediately deploys (that is, the foldable ring unfolds) for use. To assist in the deployment, a tab, pull or the like can be provided to better ensure that the user correctly removes the waste containment device from the package. After use, the user then engages the closure to close and seal the waste containment device for disposal in an appropriate receptacle.

Figure 8:
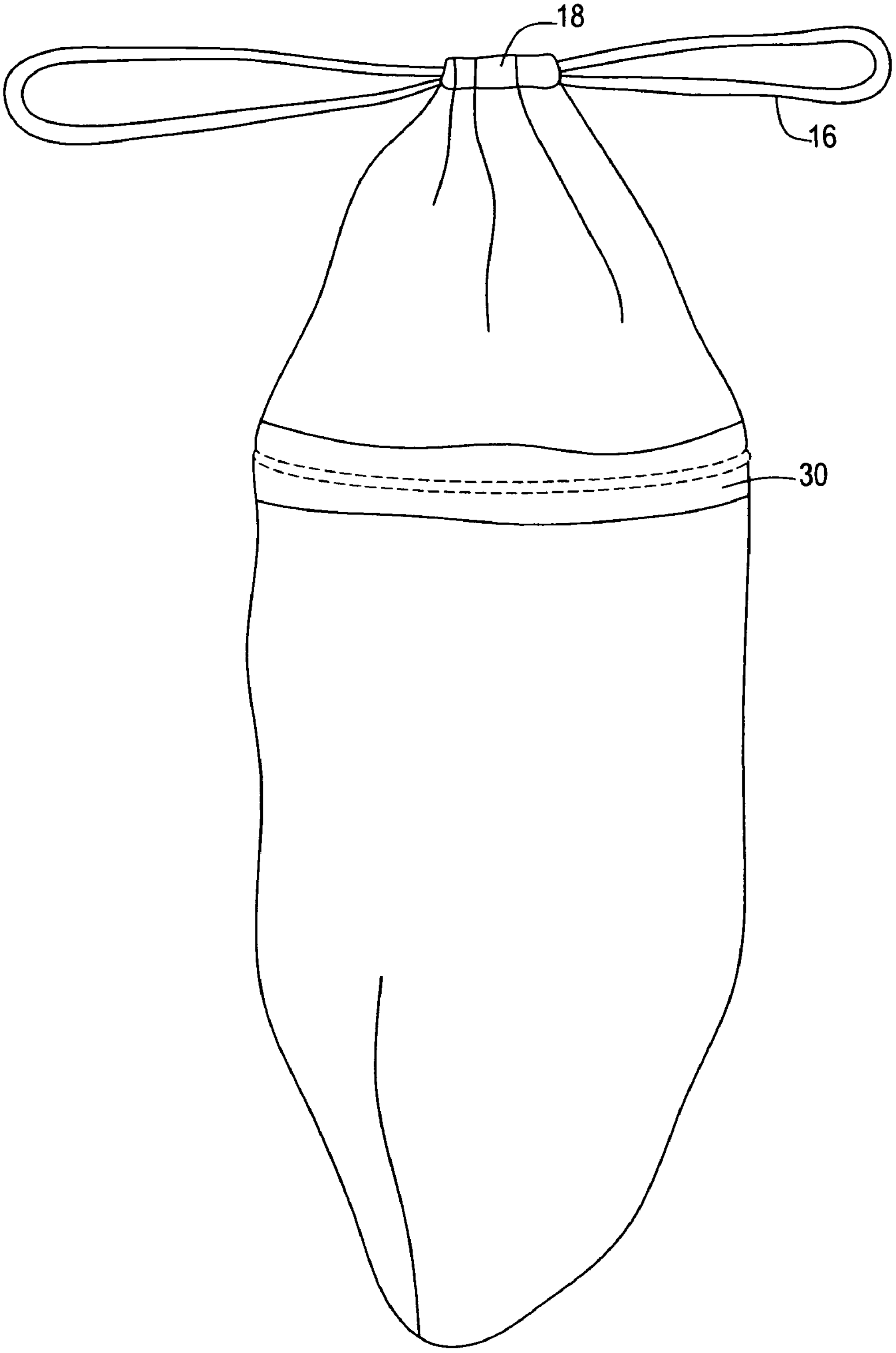
FIG. 8 illustrates a deployed waste containment device of the present invention after sealing to contain waste for disposal.

To place the waste containment device in the package for storage, the foldable ring is twisted in the shape of a "Figure 8," the two loops of the Figure 8 are brought together, superimposed (or overlapped) over one another and the entire waste containment device is placed into that package for storage. For deployment, this action happens in reverse automatically upon pulling the waste containment device out of its package. When the user removes the waste containment device from the package, the foldable ring immediately unfolds and the bag opens to form a suitable container. Significantly, when opened (or deployed) the bag moves from collapsed to being useable as a waste containment device. The user can them "aim" into the mouth of the waste containment device as needed to capture his or her vomit.

The waste containment device and system of the present invention is of an appropriate size to be carried, for example in a purse or a pocket, for use in the case of occasional vomiting episodes, such as in the case of illness or motion sickness. The present invention can also find utility in hospital settings where vomiting is more frequent. The invention provides a much more hygienic way to collect and store vomit than the "kidney bean" shaped plastic bowls or other bag-like products that are used, such as that disclosed in U.S. Pat. No. 4,610,039, the disclosure of which is incorporated herein in its entirety. The present invention can also be particularly useful for persons undergoing chemotherapy or women who are pregnant in that a packaged waste containment device (that is, the system of the present invention) can be provided in a larger package or in a dispenser that can provide an ongoing ability to contain vomit.

Additionally, the system of the present invention provides an alternative way to provide for the containment and storage of a wide-range of waste materials as discussed elsewhere herein. The ease of portability makes the system of the present invention particularly suitable for "on demand" use.

The system of the present invention can further comprise one or more dispenser systems. For example, the packaged waste containment devices can be placed in a dispenser for ready use in a hospital environment. The packaged waste containment devices can be included in vending machines, such as those in gas stations.

Turning now to the drawings, FIG. 1 illustrates the waste containment device 10 in use. Specifically, mouth 12 of the waste containment device 10 is available for use when needed, such as by a person (shown in dashed lines) who is in distress. Further illustrated on FIG. 1 is tab 14, drawstring 16, drawstring enclosure 18 and bag 20.

Figure 2:
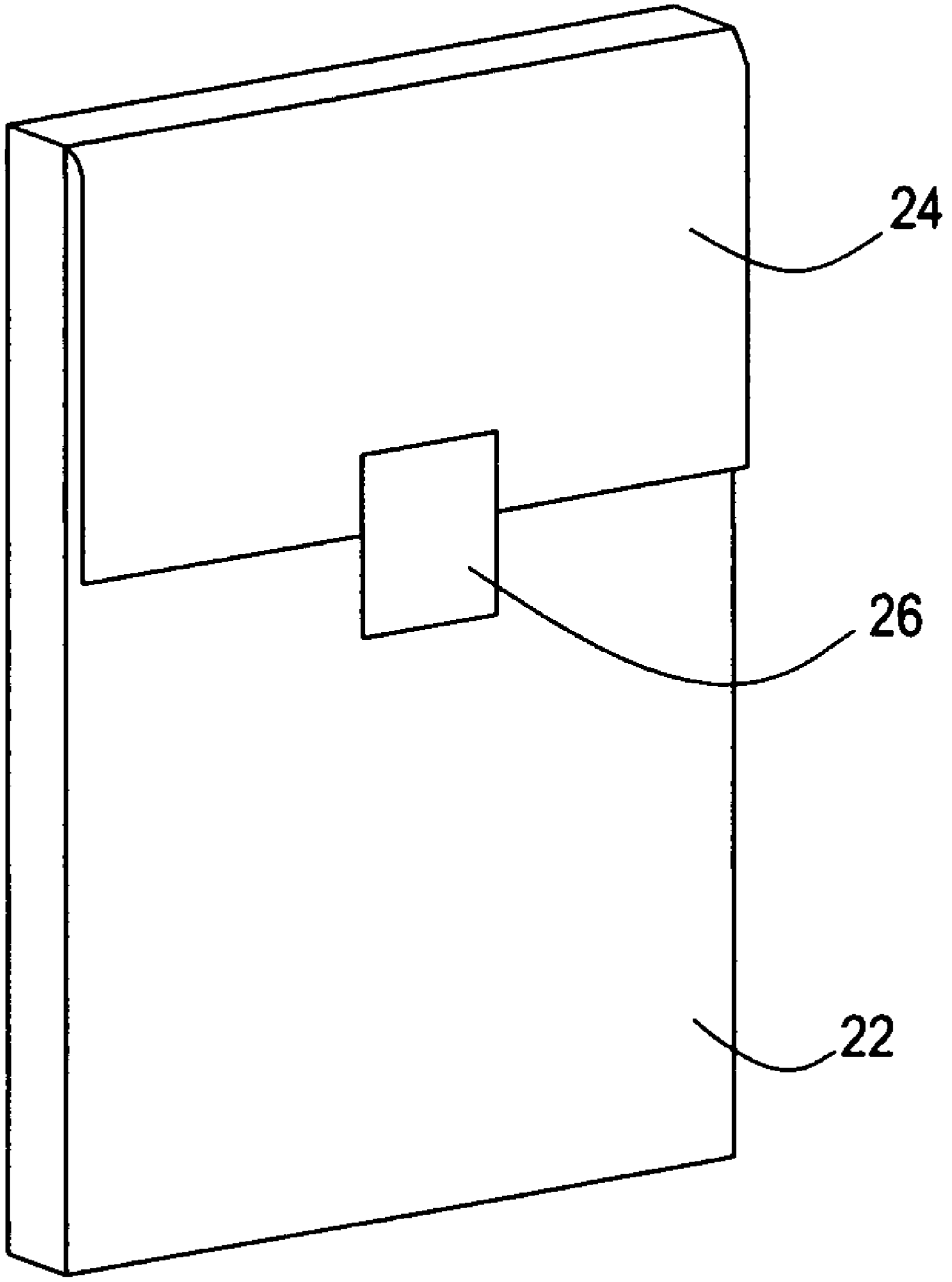
FIG. 2 illustrates one way the waste containment device of the present invention can be stored prior to deployment and use.
Figure 3:
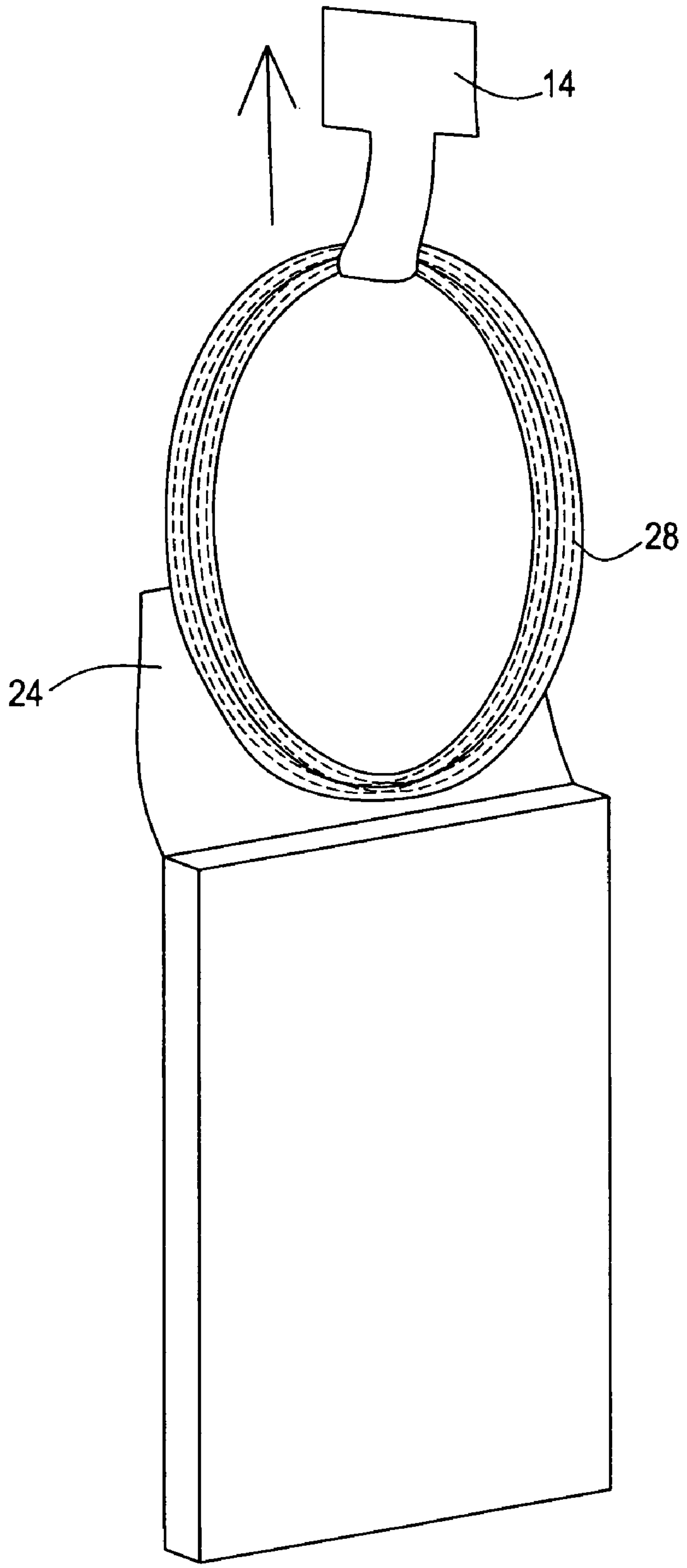
FIG. 3 illustrates a manner in which the waste containment device of the present invention can be removed from a storage position in a package.
Figure 4:
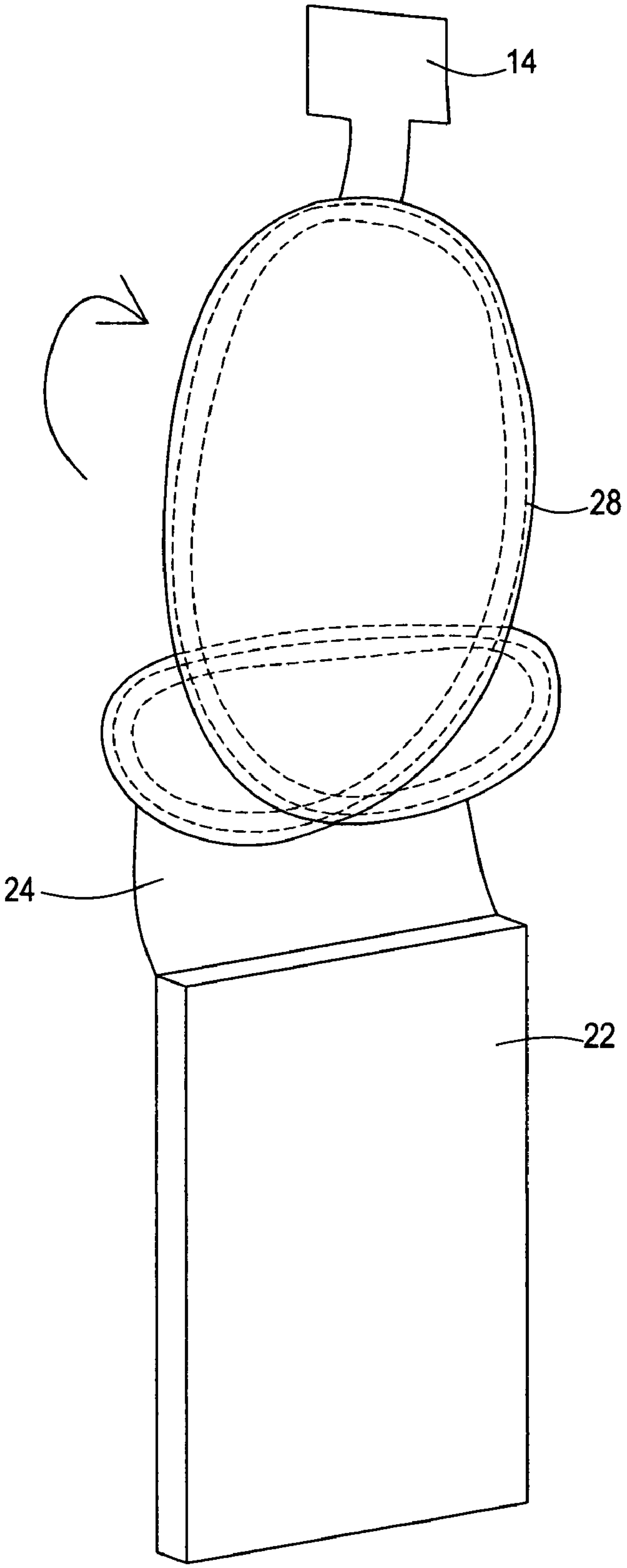
FIG. 4 illustrates the unfolding of the ring of the waste containment device of the present invention during deployment for use from a package.

FIG. 2 illustrates one form of the package 22 of that comprises one form of the waste containment device system of the present invention. The package 22 comprises a flap 24 having a closure 26. In FIG. 3, flap 24 of package 22 has been opened by the user (not shown). FIG. 3 does not show the bag so as to demonstrate the orientation of foldable ring 28 in use. FIG. 4 illustrates one manner in which foldable ring 28 deploys from package after tab 14 is pulled by a user (not shown). Again, FIG. 4 does not show the bag so as to better demonstrate the orientation of foldable ring 28 during deployment.

Figure 5:
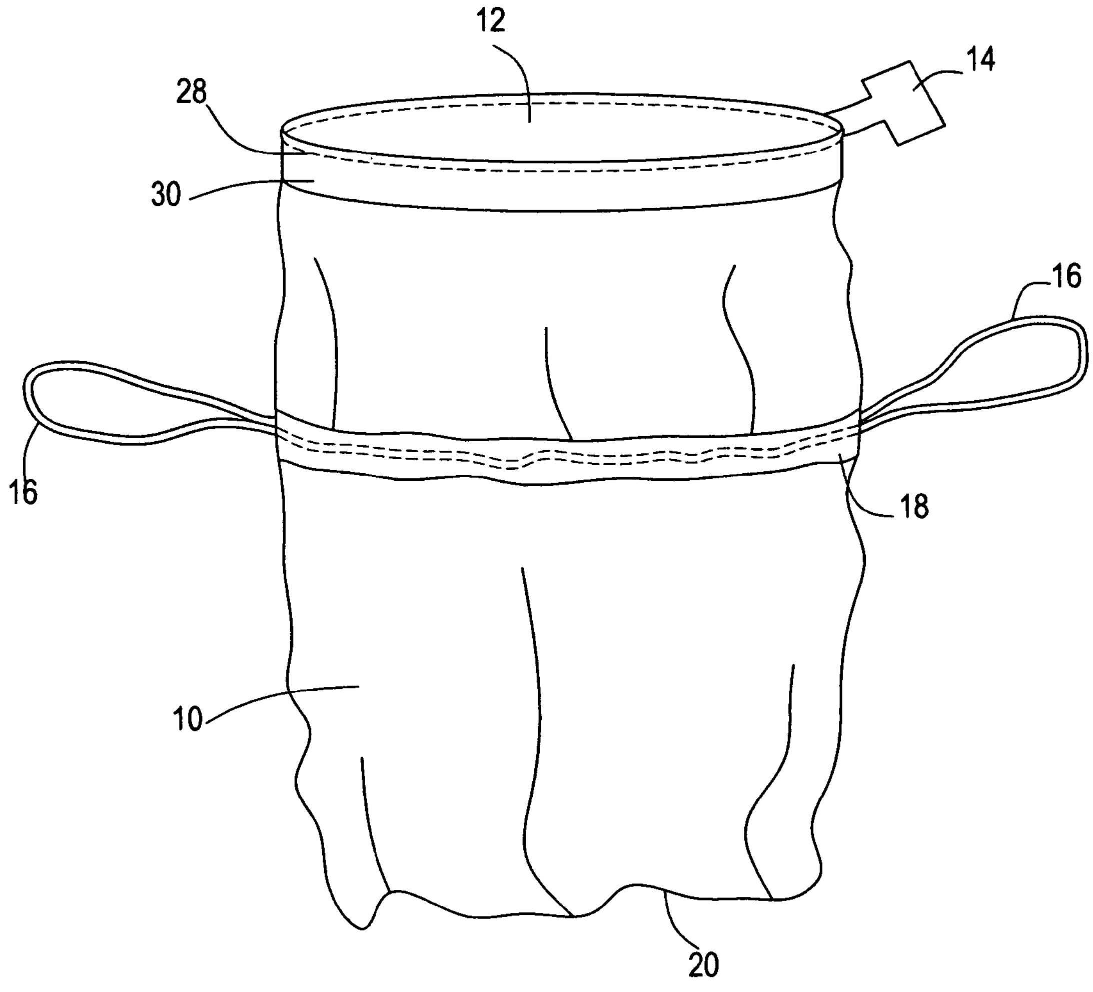
FIG. 5 illustrates a deployed waste containment device of the present invention.

FIG. 5 illustrates the deployed waste containment device 10. Drawstring 16 is situated in drawstring enclosure 18. Foldable ring 28 is shown in its deployed form as the circumference (shown in dashed lines) of waste containment device 10. Foldable ring 28 is situated in foldable ring enclosure 30. When deployed, the waste containment device 10 provides mouth 12. FIG. 5 illustrates one of the suitable configurations of the waste containment device of the present invention, others are described hereinabove.

Figure 6:
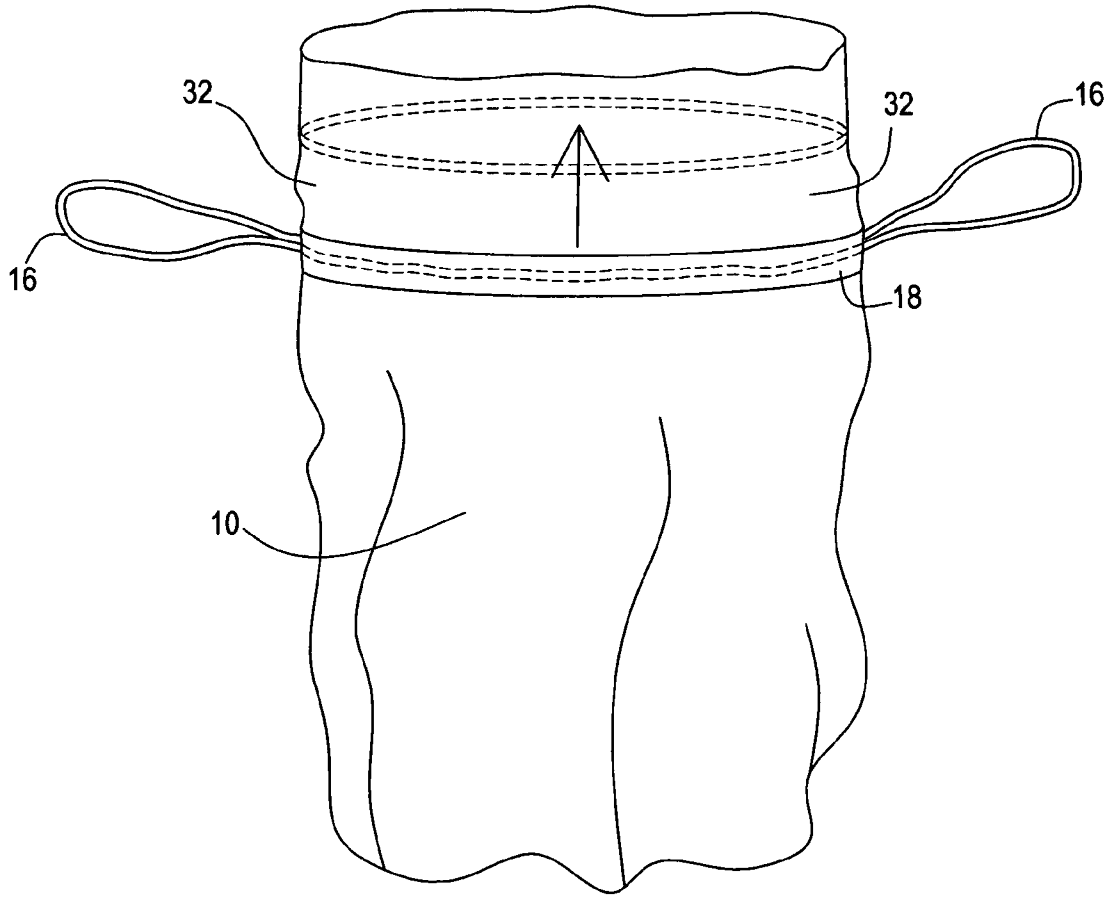
FIG. 6 illustrates a deployed waste containment device of the present invention showing a direction of movement prior to closing.
Figure 7:
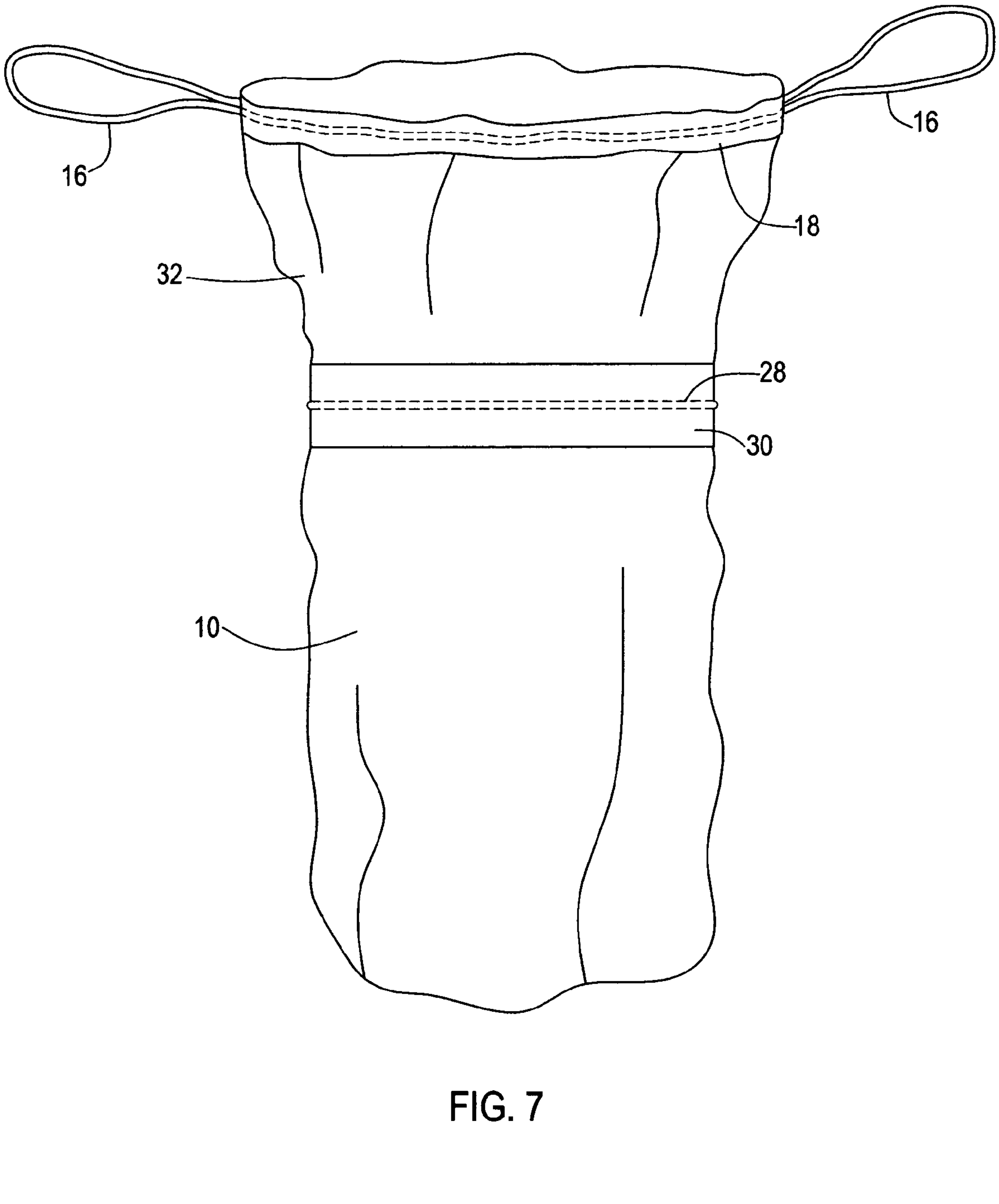
FIG. 7 illustrates a deployed waste containment device of the present invention where a drawstring is ready for sealing.

FIG. 6 illustrates one way in which waste containment device 10 can be closed by a user (not shown). Specifically, upper portion 32 of waste containment device 10 can be directed toward the direction of the arrow such that the mouth portion (shown in dashed lines) changes position with the top portion. This is further illustrated in FIG. 7, wherein drawstring 16 and drawstring enclosure 18 are now situated at a the top of waste containment device 10 and foldable ring (shown in dashed lines) and foldable ring enclosure 30 are now located below, that is, the mouth 12 is no longer situated at the top of waste containment device 10.

FIG. 8 shows a sealed waste containment device 10 wherein drawstring 16 has been engaged to seal the top of the bag when waste (not shown) is included therein for disposal.

While the invention has been described in detail, various modifications to the specific embodiment illustrated will be readily apparent to those of skill in the art. Such modifications are within the spirit and scope of the present invention defined in the appended claims.

What is claimed is:

1. A portable waste containment device comprising:

a. a foldable ring moveable between an open configuration when the ring is unfolded and a storage configuration when the ring is folded; and b. a substantially water impermeable material attached to the foldable ring so as to provide a container suitable for holding liquid or semi-liquid waste when the ring is in the open configuration wherein a frame is not present along the sides or bottom of the waste containment device, and wherein the device comprises a tab or pull attached to the foldable ring, thereby allowing the device to be deployed by a user.

2. The waste containment device of claim 1 further comprising an engageable closure, thereby providing a substantially leak-proof seal when the container comprises liquid or semi-liquid waste and the closure is engaged.

3. The waste containment device of claim 2, wherein the closure comprises a drawstring.

4. The waste containment device of claim 1, wherein a mouth is formed from the foldable ring when the ring is in the open configuration, thereby making the waste containment device suitable for the collection of vomit.

5. The waste containment device of claim 1, wherein the substantially water impermeable material comprises plastic configured to form a bag when the plastic is attached to the foldable ring.

6. The waste containment device of claim 5, wherein the plastic has a thickness of from about 0.6 to about 3.0 mils.

7. A system for containing waste comprising:

a. a portable waste containment device comprising:

i. a foldable ring moveable between an open configuration when the ring is unfolded and a storage configuration when the ring is folded; and ii. a substantially water impermeable material attached to the foldable ring so as to provide a container suitable for holding liquid or semi-liquid waste when the ring is in the open configuration, and b. a package configured to allow:

i. storage of the waste containment device when the ring is folded; and ii. deployment of the waste containment device when the waste containment device is removed for use wherein a frame is not present along the sides or bottom of the waste containment device, and wherein the device comprises a tab or pull attached to the foldable ring, thereby allowing the device to be deployed by a user.

8. The system of claim 7, wherein the waste containment device comprises an engageable closure, thereby providing a substantially leak-proof seal when the container comprises liquid or semi-liquid waste and the closure is engaged.

9. The system of claim 8, wherein the engageable closure comprises a drawstring.

10. The system of claim 7, wherein the package comprises paper, plastic or a mixture thereof.

11. A method of making a portable waste containment device comprising:

a. providing a foldable ring moveable between an open configuration when the ring is unfolded and a storage configuration when the ring is folded; and b. attaching a substantially water impermeable material to the foldable ring so as to provide a container suitable for holding liquid or semi-liquid waste when the ring is in the open configuration, wherein a frame is not present along the sides or bottom of the waste containment device, and wherein the device comprises a tab or pull attached to the foldable ring, thereby allowing the device to be deployed by a user.

12. The method of claim 11, further comprising including an engageable closure on the waste containment device, thereby providing a waste containment device having a substantially leak-proof seal when the container comprises liquid or semi-liquid waste and the closure is engaged.

13. The method of claim 12, wherein the closure comprises a drawstring.

14. The method of claim 11, wherein the substantially impermeable material comprises plastic configured to form a bag when the plastic is attached to the foldable ring.

15. The method of claim 14, wherein the plastic has a thickness of from about 0.6 to about 3.0 mils.

* * * * *